(12) United States Patent
Sundaram et al.

(10) Patent No.: US 10,696,908 B2
(45) Date of Patent: Jun. 30, 2020

(54) INTEGRATED THERMAL CRACKING AND DEHYDROGENATION PROCESS FOR OLEFIN PRODUCTION

(71) Applicant: LUMMUS TECHNOLOGY LLC, Bloomfield, NJ (US)

(72) Inventors: Kandasamy Meenakshi Sundaram, Old Bridge, NJ (US); Ronald M. Venner, Franklin Lakes, NJ (US)

(73) Assignee: LUMMUS TECHNOLOGY LLC, Bloomfield, NJ (US)

( * ) Notice: Subject to any disclaimer, the term of this patent is extended or adjusted under 35 U.S.C. 154(b) by 0 days.

(21) Appl. No.: 16/039,193

(22) Filed: Jul. 18, 2018

(65) Prior Publication Data

US 2019/0023998 A1    Jan. 24, 2019

Related U.S. Application Data

(60) Provisional application No. 62/534,101, filed on Jul. 18, 2017.

(51) Int. Cl.
| | |
|---|---|
| *C07C 4/04* | (2006.01) |
| *C07C 5/327* | (2006.01) |
| *C10G 57/00* | (2006.01) |
| *C10G 9/00* | (2006.01) |
| *C10G 9/14* | (2006.01) |

(52) U.S. Cl.
CPC ............... *C10G 57/00* (2013.01); *C07C 4/04* (2013.01); *C07C 5/327* (2013.01); *C10G 9/002* (2013.01); *C10G 9/14* (2013.01); *C10G 2300/1037* (2013.01); *C10G 2300/807* (2013.01); *C10G 2400/20* (2013.01)

(58) Field of Classification Search
None
See application file for complete search history.

(56) References Cited

U.S. PATENT DOCUMENTS

| | | | |
|---|---|---|---|
| 3,342,890 A | * | 9/1967 | Croce ................. C07C 5/48 502/328 |
| 5,220,093 A | | 6/1993 | Gartside et al. |
| 2006/0094914 A1 | | 5/2006 | Alerasool et al. |
| 2009/0054716 A1 | * | 2/2009 | Baumgartner .......... C10G 9/20 585/648 |

(Continued)

FOREIGN PATENT DOCUMENTS

WO    WO-9856740 A1 * 12/1998 ............... C07C 4/06

OTHER PUBLICATIONS

International Search Report and Written Opinion issued in corresponding International Application No. PCT/US2018/042748 dated Feb. 25, 2019 (14 pages).

*Primary Examiner* — In Suk C Bullock
*Assistant Examiner* — Alyssa L Cepluch
(74) *Attorney, Agent, or Firm* — Osha Liang LLP

(57) ABSTRACT

Embodiments disclosed herein relate to systems and processes for producing olefins and/or dienes. The systems and processes may include thermally cracking a C1-C4 hydrocarbon containing feed to produce a cracked hydrocarbon effluent containing a mixture of olefins and paraffins. The systems and processes may also include dehydrogenating the cracked hydrocarbon effluent to produce a dehydrogenated hydrocarbon effluent containing additional olefins and/or dienes.

18 Claims, 1 Drawing Sheet

(56) References Cited

U.S. PATENT DOCUMENTS

| | | | |
|---|---|---|---|
| 2011/0112344 A1* | 5/2011 | Chewter | C01B 3/22 585/302 |
| 2011/0172477 A1 | 7/2011 | Sekiguchi et al. | |
| 2014/0171704 A1* | 6/2014 | Erisken | C07C 4/04 585/303 |
| 2015/0141706 A1* | 5/2015 | Choi | C07C 7/04 568/697 |
| 2016/0326069 A1 | 11/2016 | Suriye et al. | |
| 2017/0226030 A1* | 8/2017 | Li | C10G 9/36 |

* cited by examiner

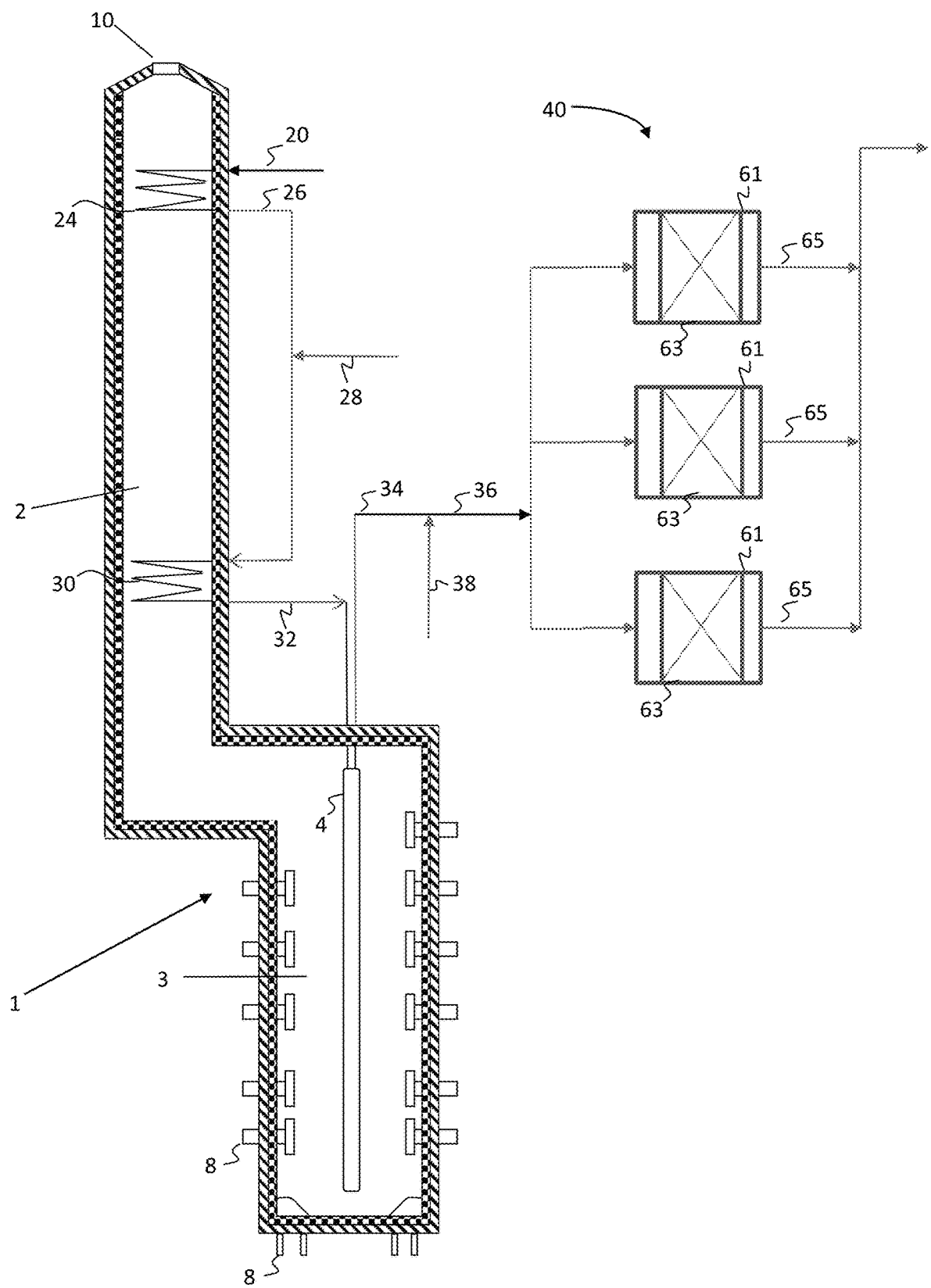

INTEGRATED THERMAL CRACKING AND DEHYDROGENATION PROCESS FOR OLEFIN PRODUCTION

BACKGROUND

To date, production of olefins from light paraffins (ethane, propane and butane) have followed one of two major routes: non-catalytic thermal cracking in the presence of steam or catalytic dehydrogenation.

Ethylene plants are designed to maximize either ethylene or propylene or sum of ethylene and propylene. The thermal route produces a mixture of targeted products (ethylene, propylene, butadiene/butenes). The mixture will vary with the selected feed and the reaction conditions. The quantity of butadiene produced in the olefins plant is generally low. Thermal crackers operate at relatively high temperatures and hence the major product is ethylene.

On the other hand, dehydrogenation units, such as CATADIENE and CATOFIN units available from Lummus Technology LLC, dehydrogenate paraffins to olefins and olefins to dienes, and these units operate at relatively low temperatures. Hence, primary olefins (propylene from propane feed, normal butene from n-butane feed, and isobutene from isobutane feed) are the main products. When normal butenes are present in the feed, butadiene is also produced. Since the equilibrium ethane conversion is very low, the conversion of ethane to ethylene does not occur to a significant level. In addition, dehydrogenation reactions are carried out at low partial pressures either by operating the unit at low absolute pressure or in the presence of inert compounds. The feed to dehydrogenation has to be heated to 500 to 650° C. to carry out the reaction to achieve economical conversions.

Historically, the route for a particular plant has been chosen based on the available feed and the desired major product due to both energy and capital cost considerations. For example, with butanes as the feed, the thermal cracking route will produce about 42% ethylene as the majority product, but the catalytic dehydrogenation route will produce close to 60% butadiene/butene product. Although reaction conditions can be varied to change these results, they do not change the target product nor do they substantially change the yields.

SUMMARY OF THE DISCLOSURE

In one aspect, embodiments disclosed herein relate to a process for producing olefins and/or dienes. The process may include thermally cracking a C1-C4 hydrocarbon containing feed to produce a cracked hydrocarbon effluent containing a mixture of olefins and paraffins. The process may also include dehydrogenating the cracked hydrocarbon effluent to produce a dehydrogenated hydrocarbon effluent containing additional olefins and/or dienes.

In another aspect, embodiments disclosed herein relate to a system for producing olefins and/or dienes. The system may include a reaction zone for thermally cracking a C1-C4 hydrocarbon containing feed to produce a cracked hydrocarbon effluent containing a mixture of olefins and paraffins. The system may also include a dehydrogenation reaction zone for dehydrogenating the cracked hydrocarbon effluent to produce a dehydrogenated hydrocarbon effluent containing additional olefins and/or dienes.

In another aspect, embodiments disclosed herein relate to a process for producing olefins and/or dienes. The process may include heating a hydrocarbon feedstock, comprising one or more C1-C4 hydrocarbons, in a convection zone of a pyrolysis reactor to form a heated hydrocarbon mixture. The heated hydrocarbon mixture may then be mixed with steam, or another inert, to form a mixed feedstock having a steam (inert) to hydrocarbon ratio in the range from 0.04 to 0.2. The mixed feedstock may then be further heated in the convection zone of the pyrolysis reactor prior to reacting the mixed feedstock in a radiant zone of the pyrolysis reactor to convert a portion of the C1-C4 hydrocarbons to produce a cracked hydrocarbon effluent containing a mixture of olefins and paraffins. The entirety of the cracked hydrocarbon effluent may then be fed to a dehydrogenation reaction zone for dehydrogenating the cracked hydrocarbon effluent to produce a dehydrogenated hydrocarbon effluent containing additional olefins and/or dienes. The dehydrogenated hydrocarbon effluent may then be separated to recover one or more fractions selected from a hydrogen fraction, a methane fraction, a C2 fraction, an ethylene fraction, an ethane fraction, a C3 fraction, a propylene fraction, a propane fraction, a C4 fraction, a butadiene fraction, a butene fraction, a butane fraction, and a C5+ containing fraction.

Other aspects and advantages will be apparent from the following description and the appended claims.

BRIEF DESCRIPTION OF DRAWINGS

The FIGURE is a simplified process flow diagram illustrating an integrated pyrolysis-dehydrogenation system for producing olefins from hydrocarbon mixtures according to embodiments herein.

DETAILED DESCRIPTION

Embodiments disclosed herein relate generally to integrated processes for the pyrolysis and dehydrogenation of hydrocarbon mixtures to produce olefins.

It has been found that an efficient integration of these two systems can provide flexibility in both target products and total production of valuable products. Carrying out the pyrolysis reaction at first with small amount of steam or without steam, to low conversions, an optimized feed to the dehydrogenation unit may be obtained. This stream may contain inerts (methane and other components which do not dehydrogenate easily) and at the same time the feed is heated sufficiently for the dehydrogenation reaction. When this stream passes through the dehydrogenation catalyst, heavier molecular weight paraffins are dehydrogenated first. Since the activity of ethane dehydrogenation is low, ethylene to ethane (reverse reaction) is also low at these temperatures. As a result, the combined pyrolysis and catalytic dehydrogenation process produces ethylene, propylene, butenes and butadiene all in higher concentration compared to individual pyrolysis or individual dehydrogenation alone.

The cracking reactor may be designed to operate at extremely low conversion and in the presence of very low steam rates and/or the absence of steam. This changes the thermal reactor design to a lower cost design and lower energy consumption design.

The products from the thermal reactor can be directly fed into the catalytic dehydrogenation reactor system. The direct feed eliminates the pre-heating step from the conventional catalytic dehydrogenation reactor system. The system benefits from a mixture of reactive and non-reactive (or low reactivity) hydrocarbons in the feed resulting in improved conversion, selectivity and total yield of valuable products. This also requires less catalyst in the catalytic reactor section.

For example, with butane feed, the total valuable products (ethylene+propylene+butadiene/butenes) will improve from a total of about 70% via conventional thermal cracker or about 65% via conventional catalytic dehydrogenation to over 80% for the integrated system.

The systems disclosed herein can also be designed to vary the split across the individual valuable products. The ability to vary feed composition, pyrolysis temperature, and dehydrogenation conditions may allow great flexibility in the resulting product mixture.

The FIGURE illustrates a simplified process flow diagram of an integrated pyrolysis and dehydrogenation system according to embodiments herein. A pyrolysis heater 1, such as a fired tubular furnace, may be used for the thermal cracking of hydrocarbons to ethylene, propylene, butenes, butadiene and other olefinic or diene compounds. The fired tubular furnace 1 has a convection section or zone 2 and a cracking section or radiant heating zone 3. The furnace 1 contains one or more process tubes 4 (radiant coils) through which a portion of the hydrocarbons fed through hydrocarbon feed line 20 are thermally cracked to produce product gases upon the application of heat. Radiant and convective heat is supplied by combustion of a heating medium introduced to the cracking section 3 of the furnace 1 through heating medium inlets 8, such as hearth burners, floor burners, or wall burners, and exiting through an exhaust 10.

The hydrocarbon feedstock 20, which may be a single hydrocarbon or a mixture of hydrocarbons, such as C1-C4 or C2-C6 hydrocarbons, may be introduced to a heating coil 24, disposed in the convection section 2 of pyrolysis heater 1 in the heating coil 24, the hydrocarbon feedstock may be heated and/or vaporized via convective heat exchange with the exhaust.

If desired, the heated hydrocarbon feedstock 26 may then be mixed with steam or an inert compound, such as nitrogen, carbon dioxide, or any other inorganic gases. The dilution steam or inert may be supplied to the process via flow line 28. Various portions of the process or additional processes in the plant may use low temperature or saturated steam, while others may use high temperature superheated steam. Steam to be used within the process or elsewhere in the plant may be heated or superheated via a heating coil (not shown) disposed in the convection zone 2 of pyrolysis heater 1.

The heated hydrocarbon mixture in stream 29 may then be fed to a heating coil 30, which may be disposed at a lower elevation in the pyrolysis heater 1, and therefore at a higher temperature, than heating coil 24. The resulting superheated mixture may then be fed via flow line 32 to one or more coils (not labeled) in the one or more process tubes 4 disposed in radiant zone 3 of pyrolysis heater 1, operated at a temperature for partial conversion, via thermal cracking, of the hydrocarbon mixture. The cracked hydrocarbon product may then be recovered via flow line 34.

The cracked hydrocarbon product may then be fed via flow lines 34, 36 to dehydrogenation reaction zone 40. Optionally, additional hydrocarbons 38 may be combined with cracked hydrocarbon product 34 for conversion in the dehydrogenation reaction zone 40. The additional hydrocarbons may include, for example, additional C2-C4 or C5 hydrocarbons, including a portion of hydrocarbon feedstock 20, for example. Depending upon the outlet temperature of the one or more coils in the one or more process tubes 4, the additional hydrocarbons may be used to cool, but not quench, the cracked effluent to a desired dehydrogenation reaction zone inlet temperature.

The hydrocarbons in flow line 36 may then be forwarded to dehydrogenation reaction zone 40, which may include one or more dehydrogenation reactors 61 operating in series or in parallel, as illustrated. The dehydrogenation reactors may each contain one or more beds 63 containing a dehydrogenation catalyst. A dehydrogenated effluent may then be recovered from reactors 61 via flow lines 65 and forwarded via flow line 67 to a product recovery and separation zone (not illustrated).

While illustrated and described above with respect to a pyrolysis heater, the thermal cracking of the feedstocks may also be performed in other types of heaters.

As described above, embodiments herein integrate pyrolysis with dehydrogenation. Carrying out the pyrolysis reaction first, with a small amount of steam or without steam, to low conversions, an optimized feed to the dehydrogenation unit is obtained. This stream may contain inert compounds (such as methane and other components which do not dehydrogenate easily) and at the same time the feed is heated sufficiently for the dehydrogenation reaction.

When this stream passes through the dehydrogenation catalyst, heavier molecular weight paraffins are dehydrogenated first. Since the activity of ethane dehydrogenation is low, ethylene to ethane (reverse reaction) is also low at these temperatures. As a result, the combined pyrolysis and catalytic dehydrogenation process produces ethylene, propylene, butenes, and butadiene, all in higher concentration compared to individual pyrolysis or individual dehydrogenation alone.

For example, when 100% normal butane is thermally cracked, approximately 20 wt % $CH_4$, 42% $C_2H_4$, 18% $C_3H_6$, 5% $C_4H_6$, 4% $C_4H_8$ and 1.2% $H_2$ (the balance other products) will be obtained at high severity. When 100% n-butane is catalytically dehydrogenated 1.3% $C_2H_4$, 4.3% $C_3H_6$, 46% normal butenes, 12.5% $C_4H_6$ and 0.6% $H_2$ (balance other products) are obtained. These are illustrative values only.

In contrast, embodiments herein may first thermally crack n-butane at low conversions (about 50%) followed by catalytic dehydrogenation, where both ethylene and propylene yields are increased. Unconverted butane in presence of these inerts reduces the effective partial pressure, which favors the dehydrogenation equilibrium to butenes and hence dehydrogenates to butenes and butadienes favorably. The pyrolysis effluents act as diluents for this reaction, lowering the effective hydrocarbon partial pressure of the main reactants and also suppressing coke formation. As a result, the calculation shows about 16% ethylene, 22% propylene and 43% butene+butadiene can be expected. Compared to catalytic dehydrogenation alone, butene+butadiene yields will be low. However, the sum of ethylene+propylene+butenes+butadiene (so called high value products) will be high compared to either pyrolysis or catalytic dehydrogenation alone. Energy consumption of embodiments herein will also be low. Since the energy used to preheat the feed for catalytic dehydrogenation is used with a small additional energy in the same heater to carry out the pyrolysis reaction, energy consumption is low. A single separation train may be used for product recovery. Therefore, the integrated scheme reduces the capital cost and reduces the energy consumption. Any light hydrocarbon feed up to C4 can be used in this scheme. This also reduces the feed preparation cost since pure butane or propane need not be produced for feed to the catalytic dehydrogenation reactor.

Judicial combination of these processes and operating at optimum conditions may thus produce a maximum amount of required olefins and diolefins with minimum amount of less valuable byproducts. The individual processes produce less quantity of olefins than the integrated process for a given quantity of C3 or C4 feed. Instead of n-butane as given in the example, one can use propane and/or propane plus butane mixtures. If isobutene is not required, isobutane can be positionally isomerized to form n-butanes and used as feed. Alternatively, isobutene product can be positionally isomerized to normal butenes, such as by using CDISIS technology, available from Lummus Technology LLC.

The above example was illustrated with 100% n-butane used as feed. Embodiments herein may use any feed, including those containing olefins, where the feed may include C1 to C4 hydrocarbons. In other words, feedstocks herein may include methane, ethane, propane, and/or butane (normal and/or iso), alone or in combinations of two or more of these. Feedstocks herein may also contain olefins, such as ethylene, propylene, and butenes. Feeds having C5+ impurities can also be used. CO2, N2 and steam, or any other inert gases, may be used as a diluent to reduce the partial pressure and increase olefin selectivity in the pyrolysis and catalytic dehydrogenation reactors.

In some embodiments the feed is first preheated, such as in a preheater used for heating feed to a catalytic dehydrogenation reactor. This heater may act as a low severity pyrolysis reactor. Alternatively, a conventional pyrolysis heater can be used for this step (as shown and described for FIG. 1). The thermal cracking reaction may be carried out, for example, at a temperature greater than is required for typical feed pre-heat to a catalytic, dehydrogenation reactor, so as to achieve the desired thermal cracking conversion. Alternatively, the thermal cracking reaction may occur over a longer residence time than is typical for pre-heat to a catalytic dehydrogenation reactor, so as to achieve the desired conversion. In other words, the integrated processes and benefits herein are not accomplished by prior art catalytic dehydrogenation processes simply by including a pre-heater to warm up the feed to catalytic dehydrogenation temperatures, where the typical preheat results in essentially no or minimal (<1%) conversion.

Typically, the pyrolysis reaction is carried out in the presence of steam. Since the conversion targeted in embodiments herein is relatively low, a small amount of steam (0.04 to 0.2 wt/wt, such as from 0.05 to 0.15 wt/wt) may be used. In some cases, the pyrolysis reaction may be carried out in the absence of steam. When inert compounds like methane (CH4) are present in sufficient quantities in the feed, a lower steam to hydrocarbon (also referred to as steam to oil, S/O) ratio can be used, and as noted earlier, may be as low as 0.

Depending upon the feed composition, a suitable low conversion may be used for the thermal cracking step. In some embodiments, a suitable conversion may be less than 10%, 10-20%, 20-30%, 30-40%, 40-50%, 50-60%, 60-70% and combinations thereof inclusive of all points therebetween. In some embodiments, for example, the conversion may be in the range from about 10% to about 70%. For para n-butane feed, for example, the target conversion will be less than 70%, such as less than 60%, or less than 55%, or less than 50%, and in some embodiments may be around 50% or between 40% and 60%. For propane rich feeds, as another example, the target conversion in the thermal cracking step may be less than 60%, such as less than 50%, and in some embodiments may be less than 40%, such as between a lower limit of 20% or 25% or 30% to an upper limit of 35% or 40% or 50%. Conversions noted herein are on a molar basis unless otherwise noted.

Depending on the feedstock used, the effluent from the pyrolysis reactor may contain H2, CH4, C2H4, C2H6, C3H6, C3H8, C4H6, C4H8, C4H10 and C5 plus. The conversion in the pyrolysis reactor may be controlled in some embodiments such that the concentration of C5+ material in the dehydrogenation reactor feed is low, such as less than 0.5 wt %, less than 1 wt %, less than 2 wt %, or less than 5 wt %, for example.

The maximum coil outlet temperature for the pyrolysis step should be kept relatively low. Radiant coil outlet temperatures (COT) may be less than 725° C., for example, and less than 675° C. is preferred. In some embodiments, the COT may be in the range from about 550° C. to about 725° C., such as from about 600° C. to about 700° C.

When higher coil outlet temperatures are used, a cold feed can be injected to cool the pyrolysis effluent to a desired temperature prior to catalytic dehydrogenation. Very high temperatures may affect the performance of the catalytic dehydrogenation catalyst. Based on the catalyst being used, the dehydrogenation feed temperature should be appropriately selected. This temperature has to be sufficient enough for carrying out the dehydrogenation reaction. Typically, this temperature (inlet to catalytic dehydrogenation reactor) is in the range from about 500° C. to about 650° C., such as in the range from about 550° C. to about 650° C. or in the range from about 500° C. to about 600°. The products coming out of the pyrolysis reactor are not componentially separated prior to catalytic dehydrogenation (as compared to separation into two or more parts of equal composition, such as via a piping tee for feeding parallel reactors).

Pyrolysis of propane and butane produce methane as a byproduct. Therefore, methane and other non-reactive species may act as a diluent for the catalytic dehydrogenation reaction. Depending upon the conversion level targeted in the dehydrogenation reactor(s), the dehydrogenation reaction can be carried out at vacuum or slightly above atmospheric pressure. The corresponding pyrolysis operating pressure may be chosen accordingly to facilitate flow from the pyrolysis reactor(s) to the dehydrogenation reactor(s).

The combined pyrolysis pre-reactor and catalytic dehydrogenation reactor can be used in a variety of catalytic dehydrogenation reactor configurations, such as cyclic reactors, continuous fixed bed reactors, moving bed reactors or fluidized bed reactors. For example, in a cyclic reactor operation (such as one having a 7 to 15 minute cycle), enough switching valves from pyrolysis to the dehydrogenation section may be provided to facilitate the transition of pyrolysis effluent flow between the reactors, as well as to provide the purge and regeneration flows. The dehydrogenation reactor will operate by switching to different reactors every 7 to 15 minutes in the cycle, followed by purge and regeneration steps prior to coming on line for dehydrogenation again. Instead of a cyclic reactor system, other fixed bed, ebullated, moving, or fluid bed dehydrogenation reactors may also be used. Embodiments herein are not limited to a particular type of dehydrogenation reactors or reactor scheme, and may include multiple types of reactors, which may be in parallel and/or series configurations.

The effluent from the dehydrogenation reactors may be processed to appropriately separate and recover the olefins and dienes. For example, one or more distillation towers may be used to separate the dehydrogenation reactor effluent into two or more fractions, such as a hydrogen fraction, a methane fraction, a C2 fraction, an ethylene fraction, an ethane fraction, a C3 fraction, a propylene fraction, a propane fraction, a C4 fraction, a butadiene fraction, a butene fraction, a butane fraction, and/or a C5+ containing fraction. If desired, a portion or all of the C5+ containing fraction(s) may be recycled for further cracking to produce additional C2-C4 olefins.

As described above, embodiments herein may produce olefins and dienes via an integrated pyrolysis and catalytic dehydrogenation process. Embodiments herein may produce a higher sum of ethylene, propylene, butene, and butadiene products compared to either pyrolysis or dehydrogenation alone. Further, the energy consumption will be relatively low, as only a small additional energy is needed compared to preheating the feed for catalytic dehydrogenation. Therefore, the integrated scheme reduces the capital costs and reduces energy consumption for the production of valuable olefins and dienes.

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed:

1. A process for producing olefins and/or dienes, the process comprising:
    thermally cracking a C1-C4 hydrocarbon containing feed to produce a cracked hydrocarbon effluent containing methane and a mixture of C2-C4 olefins and paraffins, wherein a conversion of hydrocarbons in the hydrocarbon containing feed is in a range from about 10 mol % and to 70 mol %;
    without componential separation of the cracked hydrocarbon effluent, dehydrogenating the cracked hydrocarbon effluent to produce a dehydrogenated hydrocarbon effluent containing additional olefins and/or dienes.

2. The process of claim 1, further comprising cooling the cracked hydrocarbon effluent via direct heat exchange with a hydrocarbon feed containing one or more C1-C4 hydrocarbons.

3. The process of claim 1, wherein the thermally cracking is performed in one of a pyrolysis reactor or a heat exchanger, wherein the cracked hydrocarbon effluent recovered from the pyrolysis reactor or heat exchanger is at a temperature in a range from about 550° C. to about 725° C.

4. The process of claim 3, further comprising cooling the cracked hydrocarbon effluent to a temperature in a range from about 500° C. to about 650° C. prior to dehydrogenating the cracked hydrocarbon effluent.

5. The process of claim 1, further comprising separating the dehydrogenated effluent into one or more fractions selected from a hydrogen fraction, a methane fraction, a C2 fraction, an ethylene fraction, an ethane fraction, a C3 fraction, a propylene fraction, a propane fraction, a C4 fraction, a butadiene fraction, a butene fraction, a butane fraction, and a C5+ containing fraction.

6. The process of claim 1, wherein the C1-C4 hydrocarbon-containing feed comprises n-butane, the process further comprising controlling the thermally cracking step to a conversion in the range from about 40 mol % to 60 mol %.

7. The process of claim 1, wherein the feed C1-C4 hydrocarbon-containing comprises propane, the process further comprising controlling the thermally cracking step to a conversion in the range from about 25 mol % to 40 mol %.

8. The process of claim 1, further comprising mixing steam, carbon dioxide, and/or nitrogen with the C1-C4 hydrocarbon-containing feed to form a diluted feed mixture.

9. The process of claim 8, wherein the diluted feed mixture has a diluent to hydrocarbon ratio in the range from about 0.04 to 0.2, by weight.

10. The process of claim 1, further comprising conducting the thermal cracking step at a pressure greater than the dehydrogenation.

11. The process of claim 1, further comprising conducting the thermal cracking step at a coil outlet temperature greater than a feed inlet temperature of the dehydrogenation.

12. The process of claim 1, wherein the C1-C4 hydrocarbon-containing feed comprises isobutane, the process further comprising positionally isomerizing the isobutane to form n-butanes.

13. The process of claim 1, wherein the C1-C4 hydrocarbon-containing feed comprises isobutane, the process further comprising positionally isomerizing isobutene in the dehydrogenated hydrocarbon effluent to form n-butenes.

14. A process for producing olefins and/or dienes, the process comprising:
    heating a hydrocarbon feedstock, comprising one or more C1-C4 hydrocarbons, in a convection zone of a pyrolysis reactor to form a heated hydrocarbon mixture;
    mixing the heated hydrocarbon mixture with steam to form a mixed feedstock having a steam to hydrocarbon ratio in a range from 0.04 to 0.2;
    heating the mixed feedstock in the convection zone of the pyrolysis reactor;
    reacting the mixed feedstock in a radiant zone of the pyrolysis reactor to produce a cracked hydrocarbon effluent containing methane and a mixture of olefins and paraffins;
    feeding the entirety of the cracked hydrocarbon effluent, without componential separation, to a dehydrogenation reaction zone for dehydrogenating the cracked hydrocarbon effluent to produce a dehydrogenated hydrocarbon effluent containing additional olefins and/or dienes and;
    separating the dehydrogenated hydrocarbon effluent to recover one or more fractions selected from a hydrogen fraction, a methane fraction, a C2 fraction, an ethylene fraction, an ethane fraction, a C3 fraction, a propylene fraction, a propane fraction, a C4 fraction, a butadiene fraction, a butene fraction, a butane fraction, and a C5+ containing fraction.

15. The process of claim 14, wherein the feedstock comprises n-butane, the process further comprising controlling the thermal cracking step to a conversion in a range from about 40 mol % to 60 mol %.

16. The process of claim 14, wherein the feedstock comprises propane, the process further comprising controlling the thermal cracking step to a conversion in a range from about 25 mol % to 40 mol %.

17. The process of claim 14, further comprising controlling a coil outlet temperature of the cracked hydrocarbon effluent from the pyrolysis reactor to a temperature in a range from about 660° C. to about 725° C.

18. The process of claim 17, further comprising cooling the cracked hydrocarbon effluent, via direct heat exchange with a hydrocarbon feed comprising one or more C1-C4 hydrocarbons, to a temperature in a range from about 550° C. to about 650° C., prior to dehydrogenating the cracked hydrocarbon effluent.

* * * * *